United States Patent
Sampson et al.

(10) Patent No.: US 7,867,703 B2
(45) Date of Patent: Jan. 11, 2011

(54) ELEMENT DEFINED SEQUENCE COMPLEXITY REDUCTION

(75) Inventors: Jeffrey R. Sampson, San Francisco, CA (US); Barney E. Saunders, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 297 days.

(21) Appl. No.: 10/927,809

(22) Filed: Aug. 26, 2004

(65) Prior Publication Data

US 2006/0046251 A1    Mar. 2, 2006

(51) Int. Cl.
*C12Q 1/68*    (2006.01)
*C12P 19/34*    (2006.01)
*C12M 1/34*    (2006.01)
*C07H 21/02*    (2006.01)
*C07H 21/04*    (2006.01)

(52) U.S. Cl. .................. 435/6; 435/91.2; 435/287.2; 536/23.1; 536/24.3; 536/24.33

(58) Field of Classification Search .............. 435/6, 435/287.2; 436/94; 536/23.1, 24.31, 24.33
See application file for complete search history.

(56) References Cited

U.S. PATENT DOCUMENTS

| | | | |
|---|---|---|---|
| 5,427,910 A * | 6/1995 | Kamentsky et al. ........... 435/6 |
| 6,013,440 A * | 1/2000 | Lipshutz et al. ............... 506/7 |
| 6,015,670 A * | 1/2000 | Goodfellow .................. 435/6 |
| 6,265,163 B1 * | 7/2001 | Albrecht et al. ............... 435/6 |
| RE37,891 E | 10/2002 | Collins et al. | |
| 2002/0106649 A1 | 8/2002 | Lizardi et al. | |
| 2003/0077599 A1 * | 4/2003 | Sogard ......................... 435/6 |
| 2003/0082556 A1 | 5/2003 | Kaufman et al. | |
| 2003/0096235 A1 * | 5/2003 | Dong ........................... 435/6 |
| 2003/0219772 A1 * | 11/2003 | Kuyl et al. .................... 435/6 |
| 2004/0121390 A1 * | 6/2004 | Sharma et al. ................ 435/6 |
| 2004/0132056 A1 * | 7/2004 | Su et al. ....................... 435/6 |
| 2004/0161756 A1 * | 8/2004 | Stewart et al. ................ 435/6 |

FOREIGN PATENT DOCUMENTS

WO    WO0060124 A2    10/2000

OTHER PUBLICATIONS

Invitrogen, Fast Track 2.0 RNA Isolation Kit Instructions.*
Lee, J., et al. cDNA clones coding for the heavy chain of human HLA-DR antigen. PNAS. 1982, vol. 79, pp. 545-549.

* cited by examiner

*Primary Examiner*—Bradley L Sisson

(57) ABSTRACT

A method for providing defined mixtures of nucleic acids is described. In certain embodiments, the method uses oligonucleotide probes attached to a solid support as a sequence-specific affinity agent to isolate and facilitate the amplification of defined nucleic acid fragment mixtures.

16 Claims, 4 Drawing Sheets

ELEMENT DEFINED SEQUENCE COMPLEXITY REDUCTION

FIELD OF THE INVENTION

The invention relates generally to fractionation and isolation of nucleic acids, which are useful in biological assays, and other applications. More specifically, the invention relates to obtaining defined nucleic acid fragments from complex nucleic acid mixtures.

BACKGROUND OF THE INVENTION

The isolation of discrete, sequence-defined genetic elements from complex genomic samples is an essential step in many genetic analysis protocols including, de novo sequencing, re-sequencing, gene expression, epigenetic state analyses, genetic variation discovery and scoring (e.g. SNPs and STRs). Defined sequence elements or fragments that share a common sequence element can be isolated using a common primer such as oligo dT to target the poly-A tails of messenger RNA (Chow et al., (1988) Anal. Biochem., 175; 63). Protocols to isolate and amplify defined mixtures of fragments from complex genomic samples currently rely upon defined primer pairs and some form of amplification protocol such as PCR, isothermal amplification or LCR. However, these method suffer significant limitations since the degree of multiplexing is generally limited to only 10 to 20 primer pairs which must be co-optimized for a given reaction condition. As a result, genetic analysis protocols that require the interrogation of a large number of sites or sequence elements within a complex sample mixture such as SNP genotyping or comparative genomic hybridization (CGH) have relied upon various genome complexity reduction methods that utilize various LCR, PCR and random priming techniques that are not element defined (Kinzler & Vogelstein, Nucleic Acids Res (1989) 17; 3645, Telenius et al., Genomics (1992) 13;1718, Kristjansson et al., Nature Genetics (1994) 6; 19, Lucito et al., Proc. Natl. Acad. Sci. USA (1998) 95; 4487, Kennedy et al., (2003), Nat. Biotechnol. 21;1233 & Bignell et al., (2004) Genome Research 14; 287).

What is needed is a convenient method for providing defined mixtures of nucleic acids from complex samples.

SUMMARY OF THE INVENTION

The invention addresses the aforementioned deficiencies in the art, and provides methods for isolating defined mixtures of nucleic acid fragments from complex nucleic acid samples. This method, termed "Element Defined Sequence Complexity Reduction" (EDSCR), utilizes oligonucleotides attached to a solid support such as a microarray as a highly parallel sequence-specific affinity agent to isolate and facilitate the amplification of defined nucleic acid fragment mixtures derived from complex genomic samples.

The present invention provides a method of isolating probe-defined nucleic acid fragments from a sample of nucleic acids. The method includes obtaining fragmented nucleic acids from the sample of nucleic acids. A hybridization reaction is then performed, wherein the hybridization reaction includes contacting the fragmented nucleic acids with a solid support having probes bound thereto to result in complementary fragments being retained on the solid support via the probes. The method further includes recovering the probe-defined nucleic acid fragments, wherein the recovering includes separating complementary fragments from the solid support.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods described herein and particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates the general method for performing element defined sequence complexity reduction (EDSCR).

DETAILED DESCRIPTION

Figure 1:
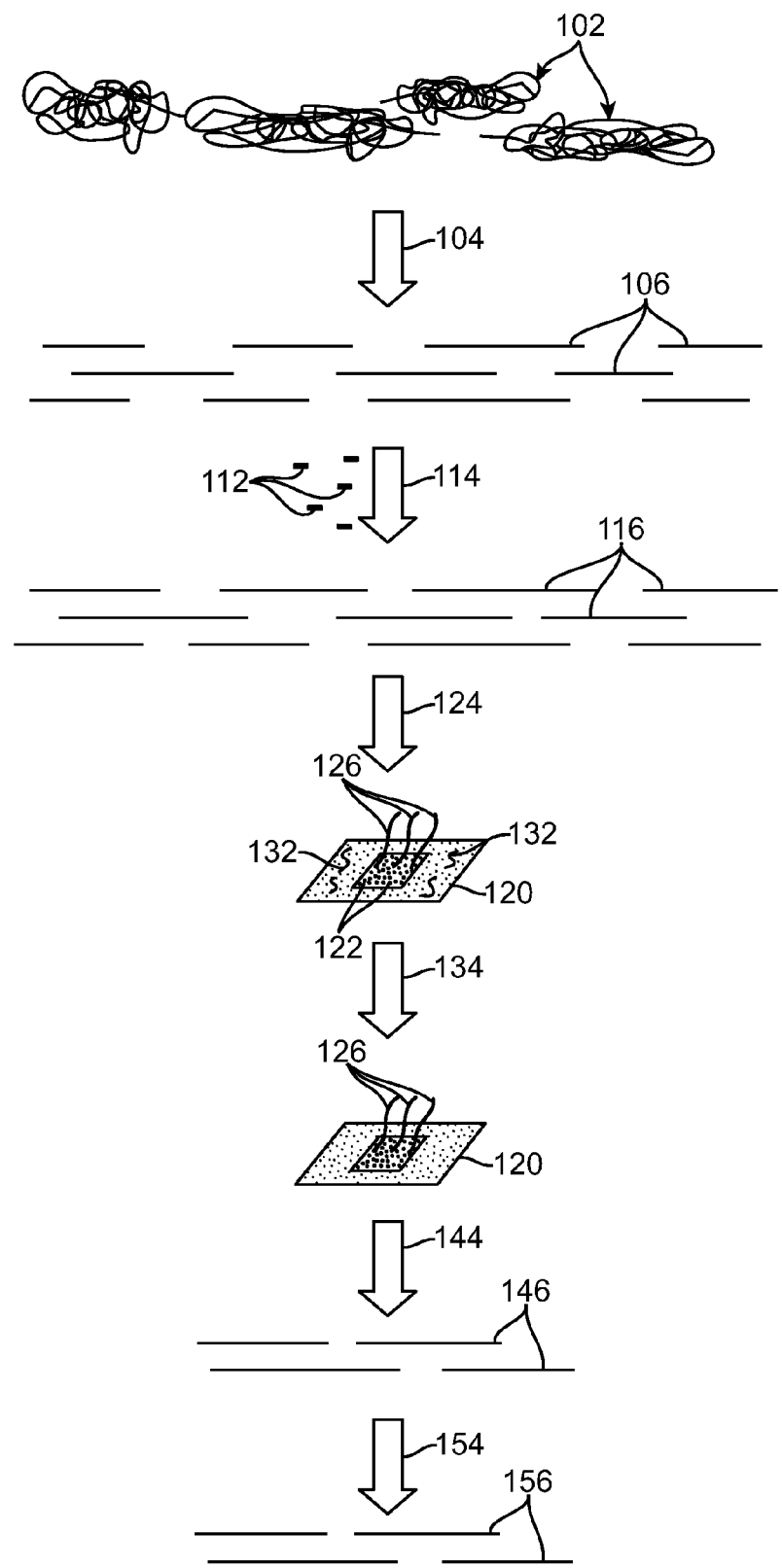

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "a solid support" includes a plurality of solid supports. In this specification and in the claims that follow, reference will be made to a number of terms that shall be defined to have the following meanings unless a contrary intention is apparent.

"Optional" or "optionally" means that the subsequently described circumstance may or may not occur, so that the description includes instances where the circumstance occurs and instances where it does not. For example, if an operation such as an amplification reaction is optionally performed it means that the amplification reaction may or may not be performed, and, thus, the description includes embodiments wherein the amplification reaction is performed and embodiments wherein the amplification reaction is not performed.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other nucleic acids that are C-glycosides of a purine or pyrimidine base, polypeptides (proteins) or polysaccharides (starches, or polysugars), as well as other chemical entities that contain repeating units of like chemical structure.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Nucleic acid fragments are nucleic acids obtained from longer nucleic acids which have been fragmented, e.g. by shearing or by enzymatic cleavage or any other method of cutting nucleic acids.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to about 100 nucleotides and up to about 200 nucleotides in length.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "oligonucleotide bound to a solid support" refers to an oligonucleotide or mimetic thereof, e.g., PNA, that is immobilized on a surface of a solid substrate, e.g. in a feature or spot of an array, where the substrate can have a variety of configurations, e.g., a sheet, bead, or other structure. In certain embodiments, the collections of features of oligonucleotides employed herein are present on a surface of the same planar support, e.g., in the form of an array.

The term "array" encompasses the term "microarray" and refers to an ordered array presented for binding to nucleic acids and the like. Arrays, as described in greater detail below, are generally made up of a plurality of distinct or different features. The term "feature" is used interchangeably herein with the terms: "features," "feature elements," "spots," "addressable regions," "regions of different moieties," "surface or substrate immobilized elements" and "array elements," where each feature is made up of oligonucleotides bound to a surface of a solid support, also referred to as substrate immobilized nucleic acids. The oligonucleotides bound to the solid support are referenced as "probes" or "probe molecules", and a nucleic acid in a mobile phase that is complementary to a probe is referenced as a "target" or a "target molecule."

The term "stringent conditions" as used herein refers to conditions that are compatible to produce binding pairs of nucleic acids, e.g., surface bound and solution phase nucleic acids, of sufficient complementarity to provide for the desired level of specificity while being less compatible to the formation of binding pairs between binding members of insufficient complementarity to provide for the desired specificity. Stringent conditions are the summation or combination (totality) of both hybridization and wash conditions.

A "stringent hybridization" and "stringent hybridization wash conditions" in the context of nucleic acid hybridization (e.g., as in array, Southern or Northern hybridizations, or immobilization to a solid support via a support-bound probe) are sequence dependent, and are different under different experimental parameters.

"Probe-defined," as in "probe-defined fragments," references a mixture of one or more nucleic acids, e.g. oligonucleotides or polynucleotides, that have been isolated by hybridizing to a collection of probes bound to a solid support, e.g. a mixture of beads or an array substrate, e.g. under stringent hybridization conditions. The isolation of the probe-defined fragments typically results in a reduced complexity mixture by removal of nucleic acids which do not bind to the array, e.g. under stringent hybridization conditions. The probes on the array may be selected to bind to any desired sequence, and typically will be selected to isolate particular fragments from a more complex mixture of fragments, e.g. a fragmented genomic DNA or nucleic acids derived from any source from which it is desired to isolate a reduced complexity set of fragments.

The present invention discloses a general method for isolating probe-defined nucleic acid fragments from complex nucleic acid samples. This method, termed "Element Defined Sequence Complexity Reduction" (EDSCR) utilizes oligonucleotides attached to a solid support such as a microarray as a highly parallel sequence-specific affinity agent to isolate and facilitate the amplification of defined nucleic acid fragment mixtures derived from complex genomic samples. The uses of the resulting defined fragment mixtures include, but are not limited to; i) generating cloned libraries having defined complexity, ii) prepare nucleic acid fragment mixtures for sequence analysis including, de novo sequencing, re-sequencing, SNP genotyping, and methylation state analysis, and iii) analyzing gene expression including discovery of rare or novel expressed genes and identifying alternative mRNA splice-site variants.

Microarrays for Use in Fragment Isolation:

A "microarray," includes any one-dimensional, two-dimensional or substantially two-dimensional (as well as a three-dimensional) arrangement of addressable regions (i.e., features, e.g., in the form of spots) bearing nucleic acids, particularly oligonucleotides or synthetic mimetics thereof (i.e., the oligonucleotides defined above), and the like. Where the microarrays are microarrays of nucleic acids, the nucleic acids may be adsorbed, physisorbed, chemisorbed, or covalently attached to the microarrays at any point or points along the nucleic acid chain.

Any given substrate may carry one, two, four or more microarrays disposed on a front surface of the substrate. Depending upon the use, any or all of the microarrays may be the same or different from one another and each may contain multiple spots or features. A typical microarray may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu m^2$, or even smaller. For example, features may have widths (that is, diameter, for a round spot) in the range from a 10 $\mu m$ to 1.0 cm. In other embodiments each feature may have a width in the range of 1.0 $\mu m$ to 1.0 mm, usually 5.0 $\mu m$ to 500 $\mu m$, and more usually 10 $\mu m$ to 200 $\mu m$. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Each feature typically includes one or more oligonucleotides bound to a substrate. Some arrays may have more than one oligonucleotide per feature, e.g. two, three, at least about 5, at least about 10, at least about 50, or at least about 100, or more, oligonucleotides per feature of the array, wherein each oligonucleotide has a different sequence from the other nucleotides of that feature. The microarray may have up to 1000 or more different probes, e.g. up to 5000 or more, up to 10,000 or more, up to 50,000 or more, or up to 100,000 or more different probes. Inter-feature areas will typically (but not essentially) be present which do not carry any nucleic acids (or other biopolymer or chemical moiety of a type of which the features are composed). Such inter-feature areas typically will be present where the microarrays are formed by processes involving drop deposition of reagents but may not be present when, for example, photolithographic microarray fabrication processes are used. It will be appreciated though, that the inter-feature areas, when present, could be of various sizes and configurations.

Each microarray may cover an area of less than 200 $cm^2$, or even less than 50 $cm^2$, 5 $cm^2$, 1 $cm^2$, 0.5 $cm^2$, or 0.1 $cm^2$. In certain embodiments, the substrate carrying the one or more microarrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With microarrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Microarrays can be fabricated using drop deposition from pulse-jets of either nucleic acid precursor units (such as monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic microarray fabrication methods may be used. Inter-feature areas need not be present particularly when the microarrays are made by photolithographic methods as described in those patents.

In certain embodiments of particular interest, in situ prepared microarrays are employed. In situ prepared oligonucleotide microarrays, e.g., nucleic acid microarrays, may be characterized by having surface properties of the substrate that differ significantly between the feature and inter-feature areas. Specifically, such microarrays may have high surface energy, hydrophilic features and hydrophobic, low surface energy hydrophobic interfeature regions. Whether a given region, e.g., feature or interfeature region, of a substrate has a high or low surface energy can be readily determined by determining the regions "contact angle" with water, as known in the art and further described in copending application Ser. No. 10/449,838 to Peck et al., filed May 30, 2003, the disclosure of which is herein incorporated by reference. Other features of in situ prepared microarrays that make such microarray formats of particular interest in certain embodiments of the present invention include, but are not limited to: feature density, oligonucleotide density within each feature, feature uniformity, low intra-feature background, low inter-feature background, e.g., due to hydrophobic interfeature regions, fidelity of oligonucleotide elements making up the individual features, microarray/feature reproducibility, and the like. The above benefits of in situ produced microarrays assist in maintaining adequate sensitivity while operating under stringency conditions required to accommodate highly complex samples.

The process of the current invention may be employed on arrays fabricated on any solid support having a surface to which chemical entities may bind. The solid support will typically comprise materials that provide support for the deposited material (e.g. the probes and any chemical modification of the surface of the solid support) and endure the conditions of the deposition process and of any subsequent treatment or handling or processing that may be encountered in the use of the solid support. Suitable solid supports may have a variety of forms and compositions and may derive from naturally occurring materials, naturally occurring materials that have been synthetically modified, or synthetic materials. Examples of suitable materials include, but are not limited to, nitrocellulose, glasses, silicas, teflons, and metals (for example, gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

In the description below, embodiments of the present invention are mostly described with reference to performing EDSCR using a microarray. However, it should be appreciated that in particular embodiments, EDSCR may be performed using a mixture of beads, each bead having a defined oligonucleotide probe analogous to that of a microarray in which each bead corresponds to a feature of the microarray. All microarray design elements are applicable to the design of the bead mixture with respect to feature density (number of beads in the mixture), probe length and location with respect to the target nucleic acids. The beads may be made of any material(s) that are compatible with the present method and that provide a surface for attachment of the probes.

A method of isolating probe-defined nucleic acid fragments from a sample of nucleic acids in accordance with the present invention is now described. The method includes obtaining fragmented nucleic acids from the sample of nucleic acids. A hybridization reaction is then performed, wherein the hybridization reaction includes contacting the fragmented nucleic acids with a solid support having probes bound thereto to result in complementary fragments being retained on the solid support via the probes. The method further includes recovering the probe-defined nucleic acid fragments, wherein the recovering includes separating complementary fragments from the solid support. Methods in accordance with the present invention will be set forth herein with reference to the Figures and the description below.

Proceeding now with reference to FIG. 1, an embodiment of the current invention is described. In FIG. 1 the general EDSCR process includes obtaining fragmented nucleic acids. In the illustrated embodiment, to obtain the fragmented nucleic acids, a sample of nucleic acids is provided, e.g. a genomic DNA sample 102. The method of the present invention can be performed using samples of nucleic acids derived from any number of sources including, but not limited to; i) genomic DNA derived from tissue, blood, whole cells, ii) pathogen DNA derived from tissue, blood, whole cells, iii) viral or phage DNA, iv) cloned DNA libraries, v) synthetic DNA libraries, vi) cDNA derived from the reverse transcription of RNA including mRNA (pre and post processed), vii) any other source of complex mixtures of nucleic acids that can be hybridized to probes bound to a solid support, and viii) any other source of nucleic acids from which it is desired to isolate nucleic acid fragments having reduced complexity.

The method illustrated in FIG. 1 proceeds as follows for obtaining fragmented nucleic acids: In the illustrated embodiment, the genomic DNA sample 102 is fragmented (indicated by arrow 104) to result in fragmented genomic DNA 106. The fragmentation 104 may be accomplished via mechanical or enzymatic methods depending upon the particular requirements of the downstream application. For example, if the downstream application can accommodate random fragments whose boundaries do not have to be location defined, then various random enzymatic or mechanical fragmentation methods can be employed. These include the treatment with Dnase 1, shearing through a syringe having a defined gauge needle, nebulization or sonication (see for example; Davidson, P. F. (1959) Proc. Natl. Acad. Sci USA, 45, 1560, Schriefer et al, (1990) Nucleic Acids Res., 18, 7455, Cavalieri and Rosenberg, (1959) J. Am. Chem. Soc., 81, 5136). Some applications however may require that the location of fragmentation be defined. In this case, the DNA can be digested with a restriction endonuclease. Depending on the choice of restriction endonuclease, the fragmented DNA may be blunt-ended or may have 3'- or 5'-overhanging termini. Selection and use of restriction endonuclease will be apparent to one of ordinary skill in the art given the disclosure herein. When using restriction endonucleases, the average length of the fragments in the final digested mixture will depend upon the enzyme used. For example, a restriction endonuclease that has a four base long recognition sequence will, on average, digest the DNA into smaller fragments ($4^4$=256-mers) than a restriction endonuclease that has a six base long recognition sequence ($4^6$=4,096-mers average length).

A number of interdependent factors should be considered in establishing the experimental design, depending on the desired application. These factors include the sequence complexity of the nucleic acids in the initial sample of nucleic acids, the desired degree of sequence complexity reduction, the number of features on the microarray, the probe lengths and the particular application in which the final reduced complexity fragment mixture will be used (see discussion below). For most embodiments, the average fragment length should be between 50 and 20,000 nucleotides, and more typically should be between 100 and 2,000 nucleotides. In general, shorter fragments will give higher degrees of hybridization specificity since they will minimize any non-specific and fragment-fragment interactions. However, when a particular genomic region does not possess a sufficiently unique sequence to serve as a probe hybridization site at or near the region of interest, it will be necessary to increase the average fragment length such that a unique site is present within the region of interest. For example, the average length of an exon in a human gene is only 120 base-pairs. If the application was directed at the isolation of defined exons from a sample comprising the entire human genome complexity, it is unlikely that it will be a high frequency event to find a probe hybridization site within the 120 base-pair target site that possesses the necessary specificity. Thus, it may be necessary to target the exon with a probe some distance from the exon thereby requiring the average fragment length to be concomitantly increased.

In the embodiment illustrated in FIG. 1, the fragmented genomic DNA 106 resulting from the fragmentation 104 are "intermediate fragments" (that is, they are subjected to further processing before being used in the next portion of the invention). After fragmentation, it may be desirable to introduce a defined or universal primer site onto the termini of the intermediate fragments. This can be accomplished by the ligation of a double stranded DNA adaptor duplex onto the termini of the genomic fragments using DNA ligase (J. Sambrook, E. F. Fritsch, & T. Maniatis, "Molecular Cloning; A Laboratory Manual" (1989), Cold Spring Harbor Laboratory Press, USA). In embodiments in which a restriction endonuclease is used to generate the fragments, the adaptor duplex may possess cohesive ends compatible with that of the genomic fragment mixture (see Saiki et al., Science (1985) 230:1350 & Lucito et al., Proc. Natl. Acad. Sci. USA (1998) 95; 4487). In the embodiment illustrated in FIG. 1, these intermediate fragments (the fragmented genomic DNA 106) are ligated (indicated by arrow 114) to DNA adaptor duplexes 112 to result in duplex terminated fragments 116. The duplex terminated fragments 116 obtained from the ligation provide the fragmented nucleic acids in the embodiment illustrated in FIG. 1

In particular embodiments the adaptor duplex 112 may comprise a unique sequence element of sufficient length to serve as a primer site for subsequent amplification of all isolated fragments. The length of the primer site within the adaptor duplex will be defined by the sequence complexity and/or sequence composition of the restriction digest mixture and is preferably between 10 and 30 nucleotides in length. It may also be desirable for some applications (see below) that the adaptor duplex comprises the recognition site for the restriction endonuclease used to generate the genomic fragments in the first step. The sequence of the restriction endonuclease recognition site on the adaptor duplex may be such that the site used to digest the genomic mixture is destroyed upon ligation of the adaptor to the genomic fragment mixture (see U.S. Pat. No. 5,093,245 to Keith et al.). In certain embodiments, the primer site also includes another restriction and/or nicking endonuclease site for use in isothermal amplification methods. In some embodiments the adaptor duplex also contains an identifier or tag sequence that can be used to either identify the identifier-sequence containing fragments or to facilitate isolation of the tag-sequence containing fragments from a more complex fragment mixture. To isolate the tag-sequence containing fragments, an affinity separation technique may be employed, wherein the affinity separation technique includes contacting the tag-sequence containing fragments with an affinity matrix having a complementary tag-recognition sequence bound to a matrix support, and then eluting the tag-sequence containing fragments. In certain embodiments the adaptor duplex may also possess a reactive moiety that allows the adaptor-containing fragment to be attached to a surface of a substrate. Such moieties include biotin, reactive amines, aldehydes, esters and the like. In such embodiments, the surface of the substrate will typically have a complementary active moiety for reacting with the reactive moiety of the adaptor duplex.

In embodiments in which an adaptor duplex 112 is ligated to the intermediate fragments (e.g. the fragmented genomic DNA 106), it may be desirable to remove any remaining unligated adaptor duplexes 112 from the ligation reaction mixture to purify the duplex terminated fragments 116. This may be accomplished by passing the ligation reaction mixture through a gel filtration column or filter membrane which possesses a suitable molecular weight cut off. The adaptor-containing fragments can also be purified by using an affinity matrix (e.g. gel or bead) containing an oligonucleotide probe complementary to a common sequence in the adaptor duplex, e.g. a tag sequence. The duplex terminated fragments 116 obtained from the purification provide the fragmented nucleic acids in the embodiment employing such a purification.

A method in accordance with the invention thus includes obtaining fragmented nucleic acids, as described above with regard to the embodiment illustrated in FIG. 1. In particular embodiments, the fragmented nucleic acids may comprise adaptor duplex terminated fragments, as described above. In certain embodiments, the fragmented nucleic acids may be obtained essentially by fragmenting a sample of nucleic acids, thereby resulting in the fragmented nucleic acids (without addition of adaptor duplexes), as described above.

In an embodiment in accordance with the present invention, the method of isolating probe-defined nucleic acid fragments includes, after obtaining the fragmented nucleic acids, performing a hybridization reaction. Performing a hybridization reaction includes contacting the fragmented nucleic acids with a solid support having probes bound thereto to result in complementary fragments being retained on the solid support via the probes. In typical embodiments, before contacting the fragmented nucleic acids with a solid support having probes bound thereto, the fragmented nucleic acids are denatured to facilitate hybridization to the probes bound to the solid substrate. The fragmented nucleic acids may denatured by any suitable process, e.g. heating to 95° C. for 10 minutes and then quickly cooling to denature the double-stranded fragments, or treating with mild base (pH 10) followed by neutralization and precipitation with ethanol (J. Sambrook, E. F. Fritsch, & T. Maniatis, "Molecular Cloning; A Laboratory Manual" (1989), Cold Spring Harbor Laboratory Press, USA).

The denatured fragment mixture is then fractionated by hybridizing the mixture to a microarray comprising a pre-defined set of oligonucleotide probes having sequences that are complementary to the DNA fragments that are to be isolated from the sample. Referring again to the embodiment illustrated in FIG. 1, the fragmented nucleic acids obtained as described above (the duplex terminated fragments 116) are contacted (indicated by arrow 124) with a solid support 120 having probes 122 bound thereto to result in complementary fragments 126 being retained on the solid support 120 via the probes 122. "Complementary fragments" references the portion of the fragmented nucleic acids that are specifically hybridized to the probes on the solid support and are retained on the solid support while subjected to the hybridization and wash conditions used while performing the hybridization reaction.

The hybridization and wash conditions used while performing the hybridization reaction are selected to provide the required hybridization specificity. The hybridization and wash stringencies are typically selected to provide stable hybridization between the microarray probes and their complementary fragments while providing for destabilization of all non-specific probe-fragment and higher order fragment-fragment interactions.

Stringent hybridization conditions typically used while performing the hybridization reaction may include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C.

Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill in the art will readily recognize that alternative but comparable hybridization and wash conditions can be utilized to provide stringent hybridization conditions.

Hybridization specificity can be further enhanced by including various carrier DNAs and/or RNAs in the hybridization mixture. The incorporation of the unique primer sites into the starting fragment mixture allows for the inclusion of modest amounts of various carrier or blocking nucleic acids in the hybridization buffer since the presence of any carrier nucleic acids in the final eluted fraction (see below) would either not be amplified in the final step of the EDSCR process or interfere with the downstream application in which the fragment mixture is to be used. For example, Cot-1 DNA and/or random N-mer oligonucleotide (e.g. random 25-mer) can be included at a concentration ranging between 0.05 and 0.5 ug/mL in the hybridization mixture.

Alternatively, the hybridization mixture could contain RNA such as yeast or *E. coli* tRNA at a concentration ranging between 0.05 and 0.5 ug/mL. In this case, any remaining carrier RNA can be easily removed by treatment of the sample with DNAse-free RNAase (J. Sambrook, E. F. Fritsch, & T. Maniatis, "Molecular Cloning; A Laboratory Manual" (1989), Cold Spring Harbor Laboratory Press, USA). Also, the Cot-1 DNA could be replaced with an RNA equivalent generated from in vitro transcription which could be easily removed by treatment of the sample with DNAse-free RNAase as described above.

In typical embodiments, such as that illustrated in FIG. 1, after contacting 124 the fragmented nucleic acids (e.g. the fragmented genomic DNA 106) with a solid support 120 having probes 122 bound thereto, non-specifically bound fragments 132 are washed (indicated by arrow 134) off the solid support 120.

The wash conditions are selected to provide the desired level of stringency for the hybridization reaction. The wash conditions may include stringent wash conditions, such as, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2× SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

Because the fragments can be amplified following elution from the solid support (see below), the hybridization and wash steps can be optimized for specificity at the expense of washing away some of the desired complementary fragments. This is possible because even in very high density microarrays (~50,000 features within a 1 cm×1 cm area), the size of each feature is such that number of probe molecules in each feature (between 10,000 and 100,000 probe molecules per $\mu m^2$) will ensure that a sufficient number of fragment molecules will remain hybridized even under very stringent conditions.

The embodiment illustrated in FIG. 1 shows the use of a microarray for performing a hybridization reaction with the fragmented nucleic acids. It is contemplated that the hybridization reaction may be performed using a mixture of beads as the solid support to which the probes are bound, instead of a microarray. In such embodiments adjustment of the reaction conditions and other experimental parameters will be apparent given ordinary skill in the art and the disclosure herein.

A method in accordance with the invention thus includes performing a hybridization reaction, wherein the hybridization reaction comprises contacting the fragmented nucleic acids with a solid support having probes bound thereto to result in complementary fragments being retained on the solid support via the probes, as described above. The fragmented nucleic acids may be denatured before the contacting occurs. In particular embodiments, the hybridization reaction is performed under stringent conditions, as described above. In certain embodiments, various carrier DNAs and/or RNAs may be added to the fragmented nucleic acids before the contacting occurs, as described above.

In an embodiment in accordance with the present invention, the method of isolating probe-defined nucleic acid fragments includes, after performing the hybridization reaction, recovering probe-defined nucleic acid fragments. Recovering probe-defined nucleic acid fragments includes separating complementary fragments from the solid support. Referring again to FIG. 1, in the illustrated embodiment after the hybridization reaction is performed (including contacting 124 and washing 134), the complementary fragments 126 being retained on the solid support 120 are separated (indicated by arrow 144) to provide the complementary fragments in solution 146, released from the solid support 120.

Complementary fragments may be separated from the solid support using any effective method to release the complementary fragments from the solid support and retrieve the complementary fragments. In an embodiment, separating the complementary fragments from the solid support includes eluting the complementary fragments with an elution buffer under conditions effective to release the complementary fragments from the solid support, and retrieving an eluant containing the complementary fragments. Conditions effective for releasing the complementary fragments typically involve washing the solid support in a low salt buffer at elevated temperatures and/or pH. This would include, but be not limited to, buffer conditions comprising 0.5×TE (pH 8 to 9.5), 0.05×SSC/0.1% SDS at a temperature ranging between 70° C. and 95° C. Denaturants such as formamide or urea will typically be included in the elution buffer to efficiently elute the complementary fragments.

In another embodiment, separating the complementary fragments from the solid support includes cleaving probes from the array to release the complementary fragments into solution, and retrieving the solution containing the complementary fragments. In one embodiment, probes are cleaved from a solid substrate such as a glass microarray substrate by treating the microarray with a basic solution (pH ~10) followed by neutralization of the solution and precipitation with ethanol to retrieve the complementary fragments. In certain embodiments the probes are bound to the solid support via a chemically cleavable moiety which is cleaved to release the probes from the solid support (releasing the complementary fragments, also) after performing the hybridization reaction. DNA fragments may also be obtained by first isolating the feature-containing region of the solid support (e.g. a microarray), crushing the microarray into a powder and then using fragment-containing powder directly in the fragment amplification reaction (below) or directly in the desired application.

In particular embodiments, the complementary fragments separated from the solid support provide the probe-defined nucleic acid fragments without further processing. In other embodiments, recovering the probe-defined nucleic acid fragments includes further processing of the complementary fragments to yield the probe-defined nucleic acid fragments. In the embodiment illustrated in FIG. 1, the complementary fragments are subjected to further processing (indicated by arrow 154) to provide the probe-defined nucleic acid fragments 156. Various methods of manipulating nucleic acids are known in the art; such methods of manipulating nucleic acids that are adapted to processing the complementary fragments to result in the probe-defined nucleic acid fragments may be employed for further processing of the complementary fragments as described herein. In certain embodiments, the further processing may include purifying the complementary fragments separated from the solid support; in such embodiments, recovering probe-defined nucleic acid fragments further comprises, after separating the complementary fragments from the solid support, purifying the complementary fragments to provide the probe-defined nucleic acid fragments. Purifying the complementary fragments may be accomplished via any suitable method, including precipitation (e.g. precipitation with ethanol under conditions of high salt concentration), affinity chromatography, ion exchange chromatography, size exclusion chromatography, or any other method adapted to purifying the complementary fragments to yield the probe-defined nucleic acid fragments. In some embodiments, the purified fragments may then be amplified in an amplification reaction or may be used directly in an application which requires probe defined nucleic acid fragments.

In some embodiments in which recovering the probe-defined nucleic acid fragments includes further processing of the complementary fragments, the further processing may include amplifying the complementary fragments. In such embodiments, recovering probe-defined nucleic acid fragments further comprises, after separating the complementary fragments from the solid support, amplifying the complementary fragments to provide the probe-defined nucleic acid fragments. Any one of a number of standard primer-dependent amplification methods, including PCR, LCR, and isothermal amplification (Walker et al., (1992) *Proc. Natl. Acad. Sci USA* 89; 392), may be used for amplifying the complementary fragments. The primers used in a primer-dependent amplification (e.g. by PCR) will typically be complementary to a primer site incorporated into an adaptor duplex ligated to the fragment termini during the ligation reaction, as described above. If an isothermal amplification is used, the restriction and/or nicking endonuclease site will be incorporated into the adaptor sequence (above).

In particular embodiments, the method of the present invention provides probe-defined nucleic acid fragments. Characteristics of the probe-defined nucleic acid fragments isolated by methods described herein will typically depend on a number of factors, including the source of the sample, the number and identity of the probes bound to the solid support, and the conditions used in the hybridization and wash, as well as other factors. Given the disclosure herein, it lies within ordinary skill in the art to determine these factors and to perform methods according to the present invention without undue experimentation. In typical embodiments, the probe-defined nucleic acid fragments include at least 5 different nucleic acid fragments, e.g. at least 10 different nucleic acid fragments, at least 50 different nucleic acid fragments, at least 100 different nucleic acid fragments, at least 500 different nucleic acid fragments, at least 1000 different nucleic acid fragments, or at least 5000 different nucleic acid fragments, or more. In certain embodiments the probe-defined nucleic acid fragments include up to about 100,000 or more different nucleic acid fragments e.g. up to about 50,000 different nucleic acid fragments, up to about 10,000 different nucleic acid fragments, up to about 50000 different nucleic acid fragments, or more.

Thus, in an embodiment of a method in accordance with the present invention, the method includes, after performing the hybridization reaction, recovering probe-defined nucleic acid fragments, wherein said recovering comprises separating the complementary fragments from the solid support. As described above, in particular embodiments, separating the complementary fragments from the solid support may include eluting the fragments with an elution buffer or may include cleaving the probes from the solid support to release the complementary fragments. In certain embodiments, after the complementary fragments are separated from the solid support, they may be purified and/or amplified to provide the probe-defined nucleic acid fragments.

In particular embodiments, the EDSCR process may be repeated multiple times (e.g. two times, three times, four times, five times or more) depending upon the required purity of the fragment pool and/or the sequence complexity of the starting sample and final desired mixture. The EDSCR process may be performed in a serial manner using a defined set of microarrays wherein each successive member of the defined set comprises a defined subset of probes from the previous microarray.

In certain embodiments, the method of the present invention further includes, after recovering the probe-defined nucleic acid fragments, performing a second hybridization reaction. In the second hybridization reaction, the probe-defined nucleic acid fragments are contacted with a second support having a second probe set bound thereto to result in probe-defined nucleic acid fragments being retained on the second support via the second probe set. In embodiments in which a second hybridization reaction is performed, the method of the present invention further includes, separating the probe-defined nucleic acid fragments retained on the second support from the second support.

In typical embodiments, the probe-defined nucleic acid fragments retained on the second support are hybridized to the second probe under stringent conditions. The probe-defined nucleic acid fragments retained on the second support are typically washed under stringent conditions to remove non-specifically bound fragments. Separating the probe-defined nucleic acid fragments retained on the second support from the second support provides probe-defined nucleic acid fragments which are defined by the second probe set (i.e. the probes in the second probe set are the probes providing the "probe-defined" aspect of the probe-defined nucleic acid fragments separated from the second support.) The second support may have essentially the same form and composition of the solid support or may have any other suitable form and composition disclosed herein with respect to the solid support. The second probe set will typically be a subset of the probes bound to the solid support. The second probe set will typically provide for reduction in sequence complexity of the probe-defined nucleic acid fragments separated from the second support as compared to the probe-defined nucleic acid fragments separated from the solid support.

As indicated above, the EDSCR process may be repeated multiple times, e.g. 3, 4, 5, or more times. In such embodiments, the method will include hybridizing to a third support having a third probe set bound thereto, a fourth support having a fourth probe set bound thereto, and a fifth support having a fifth probe set bound thereto, respectively. Each probe set will typically include a reduced set of probes from the previous iteration. The method in such embodiments includes conditions and components analogous to the earlier description pertaining to the solid support having the probes bound thereto, and performance of the methods of such embodiments will be apparent given the disclosure herein.

Microarray Probe Design Considerations:

The nucleotide length and number of microarray probes (feature density) will depend upon a variety of issues including the sequence complexity of the starting sample mixture, the overall average fragment length and the requirements of the downstream application in which the reduced complexity mixture will be used. For example, EDSCR probes can be designed to investigate specified "target-types", such as coding regions, transcription control regions, introns, intron-exon boundary regions, methylation sites, recombination sites and so forth.

While each downstream application (library creation, sequencing, etc.) or specified target-types will likely bring application or sequence element-specific criteria to the probe design, there exist some general considerations. The probe length should be sufficient to ensure specific hybridization within the boundaries of the sequence complexity of the sample mixture. In preferred embodiments, the probe lengths will be between 10 and 100 nucleotides, and more preferably between 20 and 60 nucleotides. The exact location and length of each probe with respect to either a random set of fragments or a defined restriction fragment will be determined using standard accepted design methods which account for base-pairing specificity and stability, internal probe and fragment structures, repetitive elements and potential modifications.

For many applications, it will be desirable that the probes not be too specific so that fragments which contain both known and unknown nucleotide variations (e.g SNPs, deletions and insertions) within the region complementary to probe can be isolated (see below). The rate of single nucleotide variation within the human genome is estimated at approximately 1/1250 (Venter, C. J. et al., (2001) Science 291, 1304). For example, a 20-mer probe would be sufficient to ensure the necessary fragment specificity within a mixture having a sequence complexity equal to that of the human genome. However, it is likely that any single nucleotide variation, deletion or insertion within the complementary region of the targeted fragment would prevent stable hybridization at the required fragment-specific stringency. In contrast, 60-mer probes would possess the required fragment specificity while allowing for some degree of mismatches and/or deletions thereby enabling the isolation of fragment having unknown variations at any location within the fragment.

Both the overall fragment length of the starting sample mixture and the feature density of the microarray will determine the sequence complexity of the final mixture of probe-defined nucleic acid fragments isolated using the method of the present invention. It has been shown that single nucleotide specificity can be achieved in a microarray format for sample mixtures having a sequence complexity approaching 500,000,000 base-pairs (Kennedy et al., (2003), Nat. BioTechnol. 21;1233). Moreover, recent CGH experiments with various types of microarrays indicate that fragment-specific hybridization can be achieved from samples having a sequence complexity equal to that of the entire human genome (3.2× $10^9$ base pairs) (see: U.S. patent application Ser. No. 10/744,595 to Bruhn et al.; filed Dec. 22, 2003). EDSCR is therefore useful for reducing the sequence complexity of the entire human genome (or equivalent) to any lower value in an individual element-defined manner.

In preferred embodiments, the microarray will comprise between 100 and 500,000 probe (features) where each probe comprises a sequence element that is complementary to a defined set of fragments within the sample mixture. The number of probes will depend upon the sequence complexity of the starting sample, the desired level of sequence complexity reduction and the particular downstream application in which the fragment mixture will be used.

By way of example, an array can be designed to isolate a set of fragments corresponding to a defined set of genes from a human genome sample. The mean length of an entire human gene including exons and introns is about 14,000 base-pairs. However, while the length of an exon can range from only a few base-pairs to ~500 base-pairs, the mean exon length is only about ~120 base-pairs. The mean number of exons per gene is about 7 giving a mean coding region of approximately 1,000 base-pairs (Lander E. S et al., (2001) Nature, 409, 860). Given this average gene architecture, the minimal number of probes per average gene would be 7; one for each exon. However, it may be desirable to have sufficient redundancy to ensure capture of the entire gene including intron-exon boundaries. It may also be desirable to include probes for both strands of the genome. Thus in a preferred embodiment for the capture of a defined coding region of a gene, the number of probes per average gene would range between 7 and 30 depending upon the required coverage. Thus, a microarray comprising 100,000 defined probes (30 per gene) could capture >3,000 genes from the human genome. This would correspond to approximately 10% of the total coding region of the human genome (Lander E. S et al., (2001) Nature, 409, 860, Venter, C. J. et al., (2001) Science 291, 1304). Likewise, a much smaller microarray having only ~10,000 features could capture the coding region for ~300 genes (or more, depending on the number of probes per gene).

Another example of a particular array design would be one directed at isolating a defined set of expressed genes (mRNAs) from a biological sample. In this case, the probes would be directed to a defined set of cDNAs generated from an mRNA mixture. In a preferred embodiment, the cDNAs would be full-length copies. The cDNAs comprise a contiguous set of exons with no interruption by introns, and would therefore have an average length of approximately 1,000 nucleotides (Lander E. S et al., (2001) Nature, 409, 860). The number of probes per gene would therefore depend upon the total sequence complexity of starting cDNA sample and the degree to which the cDNA mixture is fragmented. A minimum number of probes per cDNA would be one but more preferably 3 and most preferably 6. Thus, in the case of 6 probes per gene, a microarray comprising 100,000 probes could isolate >15,000 cDNA species which is equivalent to the actual number of individual mRNA species that is expressed in a cell at any given time. As discussed above, the number of probes and their location with respect to the desired genomic region will be dictated by the ability to ensure specific hybridization within the sequence complexity of the starting sample.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Use of EDSCR for Genetic Variation Discovery:

Single nucleotide polymorphisms (SNPs) are powerful genetic markers for associating specific genetic alleles with complex traits or disease. Genome-wide association studies generally rely upon a universal set of SNPs that are relatively frequent (>10%) among all or most ethnic populations. However, it is becoming increasingly clear that many disease causing or disease associated alleles are rare within the entire population, often being restricted to a particular ethnic group, defined cohort or closely related families.

Faham and coworkers (Human Molecular Genetics. (2001) 10:1657-1664) have developed a powerful method to perform high-throughput scanning of DNA sequence variations. This method, termed "Mismatch Repair Detection" (MRD), leverages the mismatch repair system of E. coli to select, for a pre-defined set of genomic fragments derived from a pool of individuals, only those fragments that contain variant sequences with respect to a reference standard sample. MRD exploits the ability of bacterial cells to co-repair long stretches of DNA in a manner that specifically selects for only those transformants that possessed a sequence variant.

A critical step in the MRD process requires the formation of heteroduplexes between a complex pool of single stranded standards comprising the genomic regions of interest and their complements derived from a pooled sample of many individuals, which may contain SNPs or other types of sequence variations. The present MRD process can accommodate thousands of different genomic fragments having a length between 300 and 500 nucleotides. This would allow for about millions of bases of genomic sequence to be scanned in a single MRD reaction. Thus it is theoretically possible to scan the entire coding and associated control regions of the human genome (~200 Mb) in just a few separate MRD reactions using current MRD protocols.

However, a current bottleneck in the MRD process is the isolation and amplification of hundreds of thousands of defined genomic fragments used to construct the standard vectors as well as the complementary fragments from the pooled cohort used to perform MRD. The protocol is currently performed, on a much smaller scale, using multiplex PCR to isolate and amplify the desired fragments. However, in order to realize the full potential of MRD, a faster and more cost-effective method for isolating and amplifying these fragments is necessary.

Figure 2A:
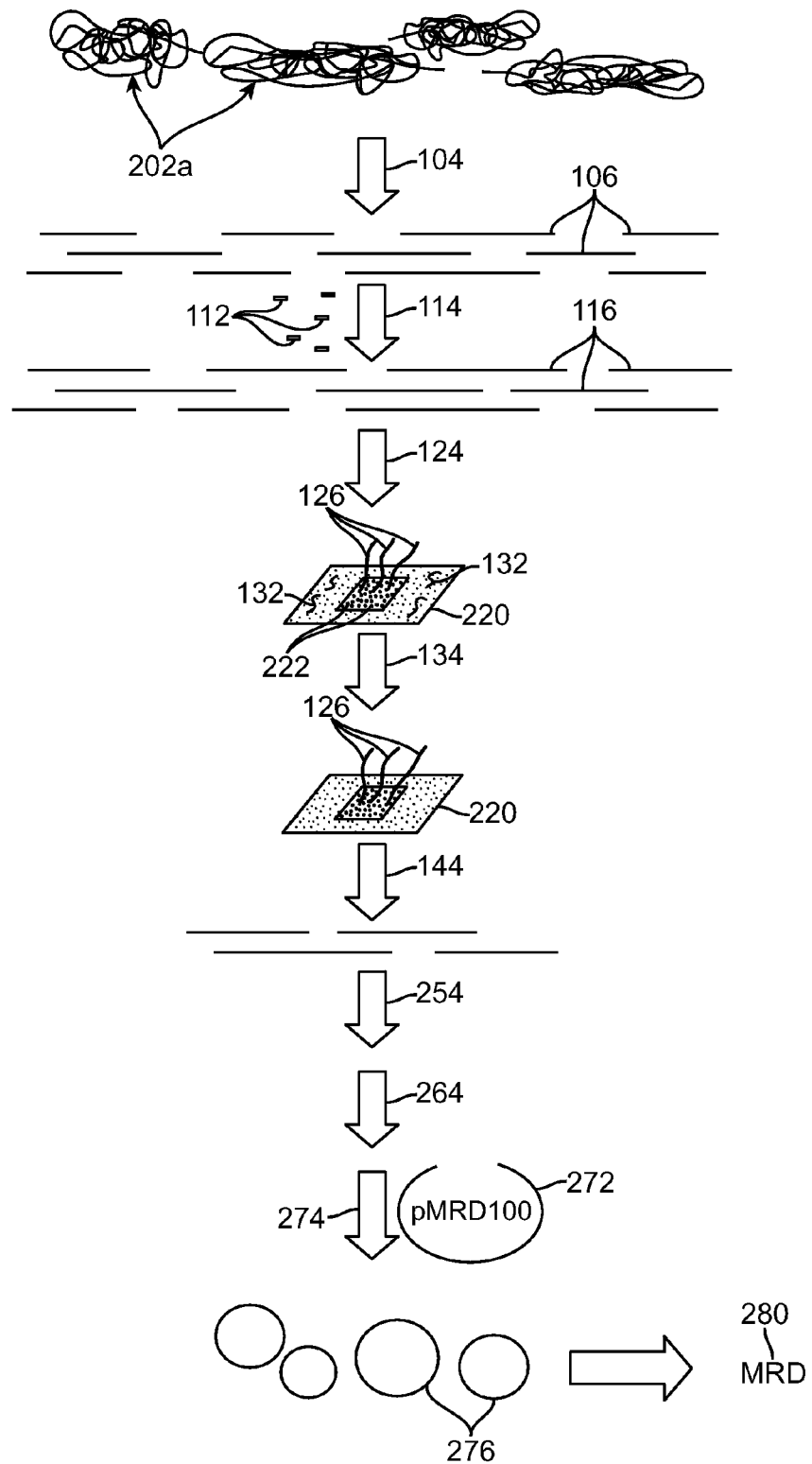
FIG. 2a shows the EDSCR method for creating a standard vector pool for Mismatch Repair Detection (MRD).
Figure 2B:
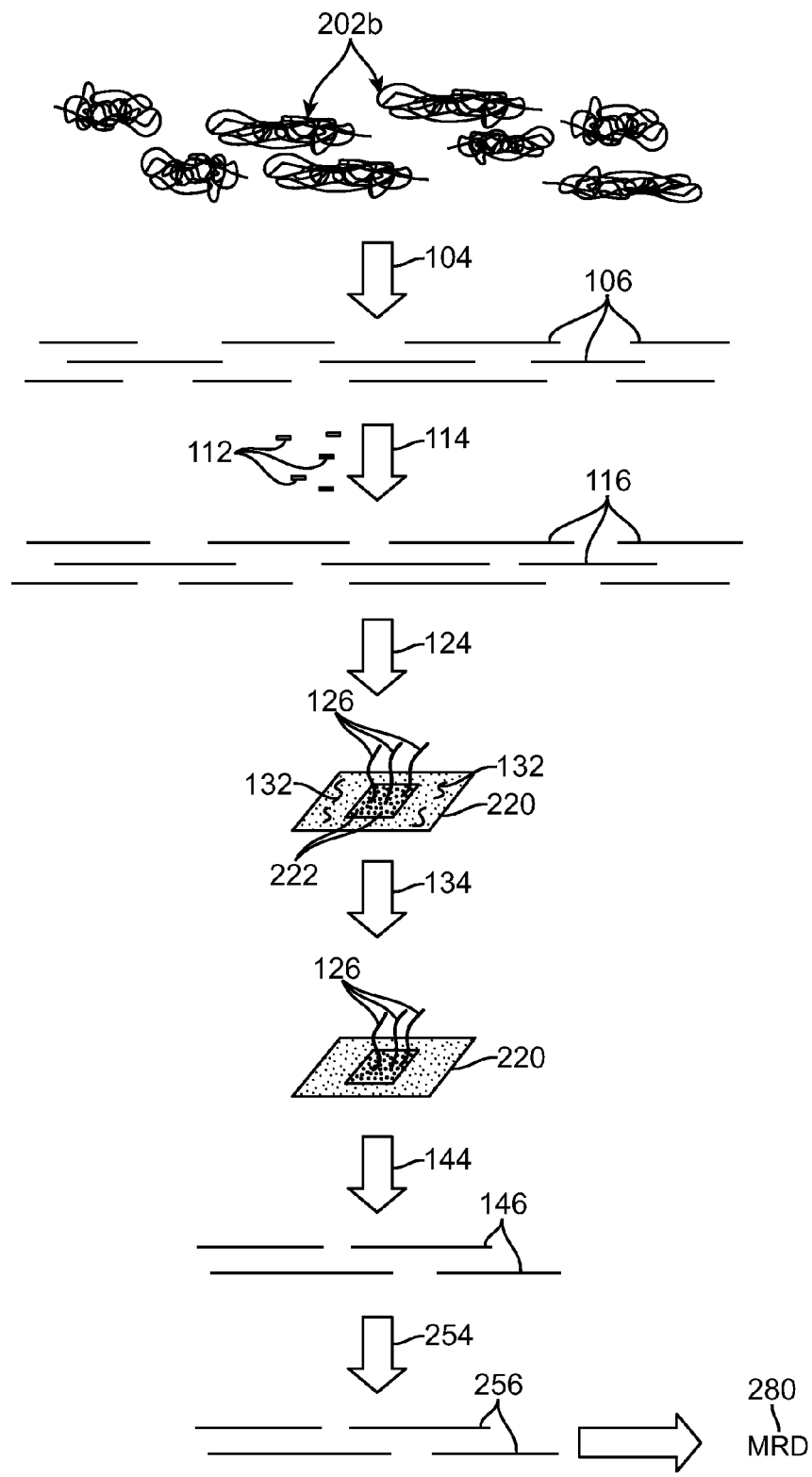
FIG. 2b shows the EDSCR method for creating a pooled experimental cohort fragment mixture for MRD.

The EDSCR process may be used in conjunction with the MRD application as outlined in FIGS. 2A & 2B. A microarray having probes directed to the desired restriction fragments comprising the genomic elements of interest would be designed and manufactured according to the criteria outlined above. The vectors (plasmids) containing the standard fragment sequences corresponding to the genomic regions of interest would then be generated by performing the EDSCR process according to FIG. 2A according using the protocols and conditions outlined above. Briefly, the standard genomic sample 202a would be fragmented (indicated by arrow 104) by digestion with a restriction endonuclease selected to produce the desired average fragment lengths and boundaries. Adaptor duplexes 112 would then be ligated (indicated by arrow 114) to the fragmented DNA 106, incorporating a common yet unique primer site for subsequent amplification. The duplex terminated fragments 116 would then be denatured and contacted (indicated by arrow 124) with the probes 222 on the microarray 220. Non-specifically bound fragments 132 would be washed 134 off the microarray 220 using stringent wash conditions. The complementary fragments 126 would then be separated (indicated by arrow 144) from the microarray 220, e.g. by elution, to give the complementary fragments in solution 146, which are then PCR amplified (indicated by arrow 254) using primers complementary to the common primer site. The resulting probe-defined nucleic acid fragment mixture would then be digested (indicated by arrow 264) with the original restriction endonuclease to recreate the original cohesive ends and then ligated (indicated by arrow 274) into the linearized pMRD 100 plasmid 272 (or equivalent) to create the final standard vector pool 276.

Referring to FIG. 2B, the pooled experimental cohort genomic DNA 202b comprising a mixture of between 10 and 1,000 individuals would then be fragmented 104 by digestion with the same restriction endonuclease as above. Adaptor duplexes 112 would then ligated 114 to the fragmented DNA 106, incorporating a common yet unique primer site for subsequent amplification. The duplex terminated fragments 116 would then be denatured and contacted 124 with the probes 222 on the microarray 220. Non-specifically bound fragments 132 would be washed 134 off the microarray 220 using stringent wash conditions. The complementary fragments 126 would then be separated 144 from the microarray 220, e.g. by elution, to give the complementary fragments in solution 146, which are then PCR amplified (indicated by arrow 254) using primers complementary to the common primer site. The resulting probe-defined nucleic acid fragment mixture 256 is then used in combination with the standard vector pool 276 (see FIG. 2A) to perform the MRD process 280 as outlined by Faham and coworkers (Human Molecular Genetics. (2001) 10:1657-1664).

Use of EDSCR for Ultra High Throughput Sequencing:

A number of novel methods for ultra high throughput DNA sequencing are currently under development. Many of these emerging technologies are based on the analysis of single nucleic acid molecules or clonally amplified versions thereof (for reviews see: J. Shendure et al., Nature Reviews (2004) 5: 335-345; A. Marziali and M. Akeson, Ann. Rev. Biomed. Engineering (2001) 3: 195-223). These methods include i) the translocation of single nucleic acid molecules through some type of nanopore or nanochannel (Akeson, M., et al., (1999) Biophysics, 77, 3227), or ii) some stepwise chemical or fluorescence-based sequencing of spatially arrayed single molecules or beads containing multiple copies thereof (Levene, M. J. et al., (2003) Science, 299, 682; Braslavsky, I., et al., (2003) Proc. Natl. Acad. Sci. USA, 100, 396; Smith, T., (2004) Drug Discovery Today; Targets, 3, 112). In both types of approaches, a high multiplicity of nucleic acid fragments is needing to be sequenced either in serial or highly parallel manner. Moreover, most methods require some type of modification of the fragments (e.g. adaptor ligation) in order to facilitate the amplification, surface attachment or the particular sequencing chemistry (e.g. sequencing by synthesis). However, as discussed above, there currently exists no effective method for generating the required defined mixture of nucleic acid fragments starting from a high sequence complexity mixture such as an entire genome.

Figure 3:
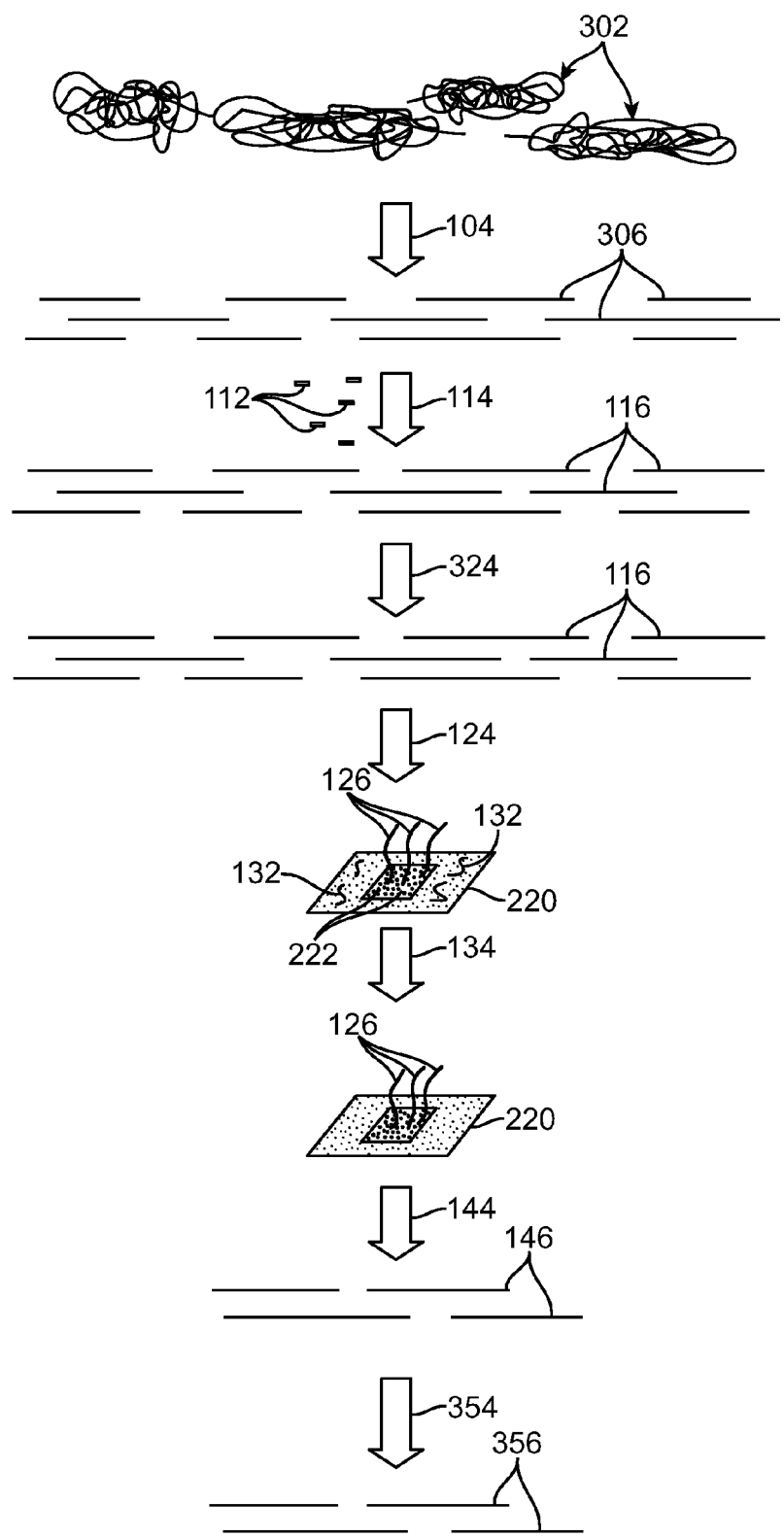
FIG. 3 depicts the EDSCR method for reducing the complexity of a genomic sample for DNA sequence analysis To facilitate understanding, identical reference numerals have been used, where practical, to designate corresponding elements that are common to the Figures. Figure components are not drawn to scale.

The present invention, EDSCR, is a novel approach to effectively generate the desired DNA mixture having the required modifications to enable the ultra high throughput sequencing process. For this application, the EDSCR process is carried out essentially as described above and outlined in FIG. 3. A microarray having probes directed to the genomic elements of interest would be designed and manufactured according to the criteria outlined above. A genomic sample 302 would then be randomly fragmented 104 to an average length dictated by the criteria outlined above to provide a mixture of fragmented DNA 306. Adaptor duplexes 112 containing the appropriate sequencing and/or amplification primer site would then be ligated 114 to the mixture. If the sequencing method requires the covalent attachment of the individual DNA fragments to a solid-support, then the appropriate chemical moiety (e.g. active amines, aldehydes, esters, biotin) would be incorporated into the adaptor duplex 112. The mixture may then optionally be enriched 324 for those fragments containing the necessary adaptor sequences. These duplex terminated fragments 116 would then be denatured and contacted 124 with the probes 222 on the microarray 220. Non-specifically bound fragments 132 would be washed 134 off the microarray 220 using stringent wash conditions. The complementary fragments 126 would then be separated 144 from the microarray 220, e.g. by elution, to give the complementary fragments in solution 146. If necessary for the desired sequencing application, the complementary fragments in solution 146 may then be amplified in an amplification reaction (indicated by arrow 354), e.g. PCR, LCR, or isothermal amplification, using primers complementary to the common primer site if necessary. The resulting probe-defined nucleic acid fragments 356 may then used in accordance with the specific process of the sequencing method employed. In various embodiments the sequencing method may involve attaching the probe-defined nucleic acid fragments to a planar surface. In some embodiments, the sequencing method may involve attaching the probe-defined nucleic acid fragments to beads followed by clonal amplification (e.g. via PCR or emulsion PCR). In certain embodiments the probe-defined nucleic acid fragments are sequenced in solution (not bound to a surface).

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method of nucleic acid sample analysis, comprising:
   a) fragmenting a sample of genomic DNA from a cell to obtain fragmented double-stranded genomic nucleic acids, wherein said fragmenting is done by shearing, nebulizing or sonicating;
   b) ligating, using DNA ligase, a double-stranded adaptor duplex comprising a primer site to both ends of said fragmented double-stranded genomic nucleic acids to produce adaptor-ligated nucleic acids;
   c) hybridizing said adaptor-ligated nucleic acids with a solid support having nucleic acid probes bound thereto to result in complementary fragments being retained on the solid support via the probes;
   d) washing the solid support to provide a washed solid support comprising said complementary fragments;
   e) subjecting said washed solid support to conditions sufficient to separate all complementary fragments retained on said washed solid support via said probes from the washed solid support to produce a reduced complexity mixture that is made up of said complementary fragments;
   f) amplifying said complementary fragments of said mixture using a primer that binds to said primer site of the adaptor duplex at both ends of said complementary fragments to produce an amplified nucleic acid sample comprising amplified nucleic acids; and
   g) sequencing said amplified nucleic acids.

2. The method of claim 1, wherein the adaptor duplex comprises a reactive moiety for binding the fragmented nucleic acids to a substrate having a surface-bound complementary active moiety for binding with the reactive moiety.

3. The method of claim 1, wherein the hybridizing is done under stringent conditions.

4. The method of claim 1, wherein the solid support having probes bound thereto is a microarray.

5. The method of claim 4, wherein the solid support comprises a planar support comprising one or more substrate materials selected from glass, silicas, metals, teflons, and polymeric materials.

6. The method of claim 1, wherein the solid support having probes bound thereto comprises a mixture of beads, each bead having one or more probes bound thereto.

7. The method of claim 6, wherein the mixture of beads comprises one or more substrate materials selected from nitrocellulose, glass, silicas, teflons, metals, and polymeric materials.

8. The method of claim 1, wherein said solid support comprises from 2 to 2,000,000 probes.

9. The method of claim 1, wherein said nucleic acid probes are bound to said solid support in features that are at a density of up to 100,000 per 1 $mm^2$.

10. The method of claim 1, wherein 10 to 100,000 different probes are bound to the solid support.

11. The method of claim 1, wherein between 100 and 500,000 different probes are bound to the solid support.

12. The method of claim 1, further comprising adding carrier DNA and/or carrier RNA to the fragmented nucleic acids of said composition of fragmented nucleic acids prior to hybridizing with said solid support.

13. The method of claim 1, wherein said conditions comprise elution of the complementary fragments retained on said washed solid support.

14. The method of claim 1, wherein amplifying the complementary fragments comprises performing an amplification reaction selected from PCR, LCR, or isothermal amplification.

15. The method of claim 1, wherein said conditions of step e) are sufficient to cleave said probes from the washed solid support.

16. The method of claim 13, wherein said elution comprises washing in a buffer at a pH of 8 to 9.5 and a temperature of 70° C. to 95° C.

* * * * *